United States Patent [19]

Lerman

[11] Patent Number: 4,520,801
[45] Date of Patent: Jun. 4, 1985

[54] CERVICAL COLLAR

[76] Inventor: Max Lerman, 1950 Carla Ridge, Beverly Hills, Calif. 90210

[21] Appl. No.: 511,841

[22] Filed: Jul. 8, 1983

[51] Int. Cl.³ ............................................... A61F 5/01
[52] U.S. Cl. ...................................... 128/75; 128/87 B
[58] Field of Search ................. 128/75, 87 B, DIG. 23

[56] References Cited

U.S. PATENT DOCUMENTS

| 3,024,784 | 3/1962 | Monfardini | 128/75 |
|---|---|---|---|
| 3,042,027 | 7/1962 | Monfardini | 128/75 |
| 3,075,521 | 1/1963 | Grassl | 128/75 |
| 3,135,256 | 6/1964 | Gruber | 128/75 |
| 3,285,243 | 11/1966 | Yellin | 128/75 |
| 3,313,297 | 4/1967 | Applegate et al. | 128/75 |
| 3,756,226 | 11/1973 | Calabrese et al. | 128/75 |
| 3,916,885 | 11/1975 | Gaylord, Jr. | 128/75 |
| 4,099,523 | 7/1978 | Lowrey | 128/75 |

*Primary Examiner*—John D. Yasko
*Attorney, Agent, or Firm*—Christie, Parker & Hale

[57] ABSTRACT

A cervical collar has front and rear halves for resting on the shoulders and extending around the neck to support the chin and rear of the patient's head. The front half through an angle is split into upper and lower sections hinged to pivot relative to each other. The upper section has a U-shaped portion conforming to the shape of the patient's chin and extending along opposite sides of the lower jaw. A U-shaped bridge member on the upper section extends downwardly below the lower jaw and across the front of the neck region. The lower section extends around the lower front portion of the patient's neck and overlies the collarbone region and the central portion of the upper chest region. Fasteners extend through guide slots in the bridge member to provide means for guiding angular travel between the upper and lower sections. The fasteners can be loosened to permit angular travel and tightened to hold the upper and lower sections in a preset angular position to conform to different neck sizes. The bridge member bridges the space between the chin-supporting upper section and the lower section to add rigidity to the chin-supporting portion of the collar. Flexible straps with Velcro fasteners on the rear half are attached to cooperating Velcro fasteners on the front half to hold the collar in place around the patient's neck.

12 Claims, 3 Drawing Figures

CERVICAL COLLAR

BACKGROUND OF THE INVENTION

1. Field of the Invention

This invention relates to an improved cervical collar.

2. Description of Prior Art

In the past, there have been different types of cervical collars used on patients who have suffered neck injuries. The cervical collar provides rigid support for the cervical vertebrae to immobilize the vertebrae while relieving pressures on cervical nerves by supporting the head and preventing undue pressures from being applied to the neck. A cervical collar should maintain front-to-back stability of the patient's head in addition to preventing rotation of the head.

Since a cervical collar may be worn by a patient over a long period of time, it is important for the cervical collar to be comfortable. It is also desirable for the cervical collar to be adjustable to adapt to various neck sizes, while maintaining the required rigid support in different adjustable positions. An adjustable cervical collar is more useful if it can be applied quickly and easily while adjusting to various neck sizes, rather than being a customed-made or custom-adjusted device.

A popular cervical collar, known as the Philadephia collar, is disclosed in U.S. Pat. No. 3,756,226 to Calabrese et al. The Philadelphia collar is formed in two halves and each half is made from a closed cell polymeric material such as polyethylene or polyurethane. The closed cell material is desirable because it can be formed in the desired shape in a die or mold and it makes the collar reasonably light in weight. However, the collar is not comfortable when worn for long periods of time. The closed cell material does not "breathe" and when a closed cell collar is worn for long periods, it can cause the patient to perspire and can cause heat rashes or other skin problems. Closed cell materials do not "breathe" in the sense that they are resistant to air circulation through them and they do not absorb fluids. Large air holes in the front and rear halves of the Philadelphia collar provide some air circulation to the skin, but the closed cell material still resists proper air circulation, fluid absorption and heat dissipation that would otherwise make the collar comfortable during prolonged use.

The present invention provides a cervical collar which is more comfortable to wear for long periods than the Philadelphia collar. The cervical collar of this invention is made, in part, from an open cell foam material which breathes during use and therefore does not create skin problems or other discomfort when the collar is worn for long periods of time.

Open cell materials are not capable of being molded to the desired anatomical shape as are closed cell materials. However, the cervical collar of this invention is made so that the open cell material can be supported in the desired anatomical shape to provide the comfort not provided by a closed cell material; and yet the cervical collar of this invention provides the necessary comfort while also providing the required support for the patient wearing the collar and while being adjustable to various neck sizes without requiring the collar to be custommade.

SUMMARY OF THE INVENTION

One embodiment of the cervical collar has front and rear halves, each being generally U-shaped and being adapted for attachment to each other for supporting the chin region and the back of the patient's head. The invention is directed principally to the front half of the cervical collar which includes a preformed semi-rigid shell in the anatomical shape that conforms to the chin region of the patient. The inside face of the shell has a resilient open cell layer on the side for contact with the chin region of the patient. The shell is split into upper and lower sections which are movable relative to each other to widen or narrow the split for adjusting to the size of the patient's neck. A generally U-shaped reinforcing bridge member extends along the split and bridges the distance between the upper and lower sections of the shell. Fastening means hold the bridge member in a fixed position relative to the upper and lower sections for adjustably holding the upper and lower portions in a desired adjustable position. In its preset position, the bridge member provides support for the chin-supporting upper section of the shell.

In one embodiment, the bridge member is part of the chin-supporting upper section of the shell. The bridge member is arranged so that its lengthwise stiffstiffness provides rigid support for the chin-supporting section of the shell in all adjusted positions of the collar.

The semi-rigid preformed upper and lower sections of the shell facilitate use of the open cell material for padding, which makes the collar comfortable for the user during long periods of use. In addition, the spacing between the upper and lower sections is quickly and easily adjustable to conform to the patient's neck size. The fasteners are simply loosened to move the upper or lower section of the collar to the desired preset position. The fasteners are then tightened to hold the bridge member in a fixed position for holding the upper and lower sections of the collar in the preset position. In that position, the bridge member provides support for the patient's chin region independently of the setting of the collar size.

These and other aspects of the invention will be more fully understood by referring to the following detailed description and the accompanying drawings.

DRAWINGS

FIG. 1 is a perspective view showing front and rear halves of a cervical collar according to the principles of this invention.

DETAILED DESCRIPTION

Figure 2:
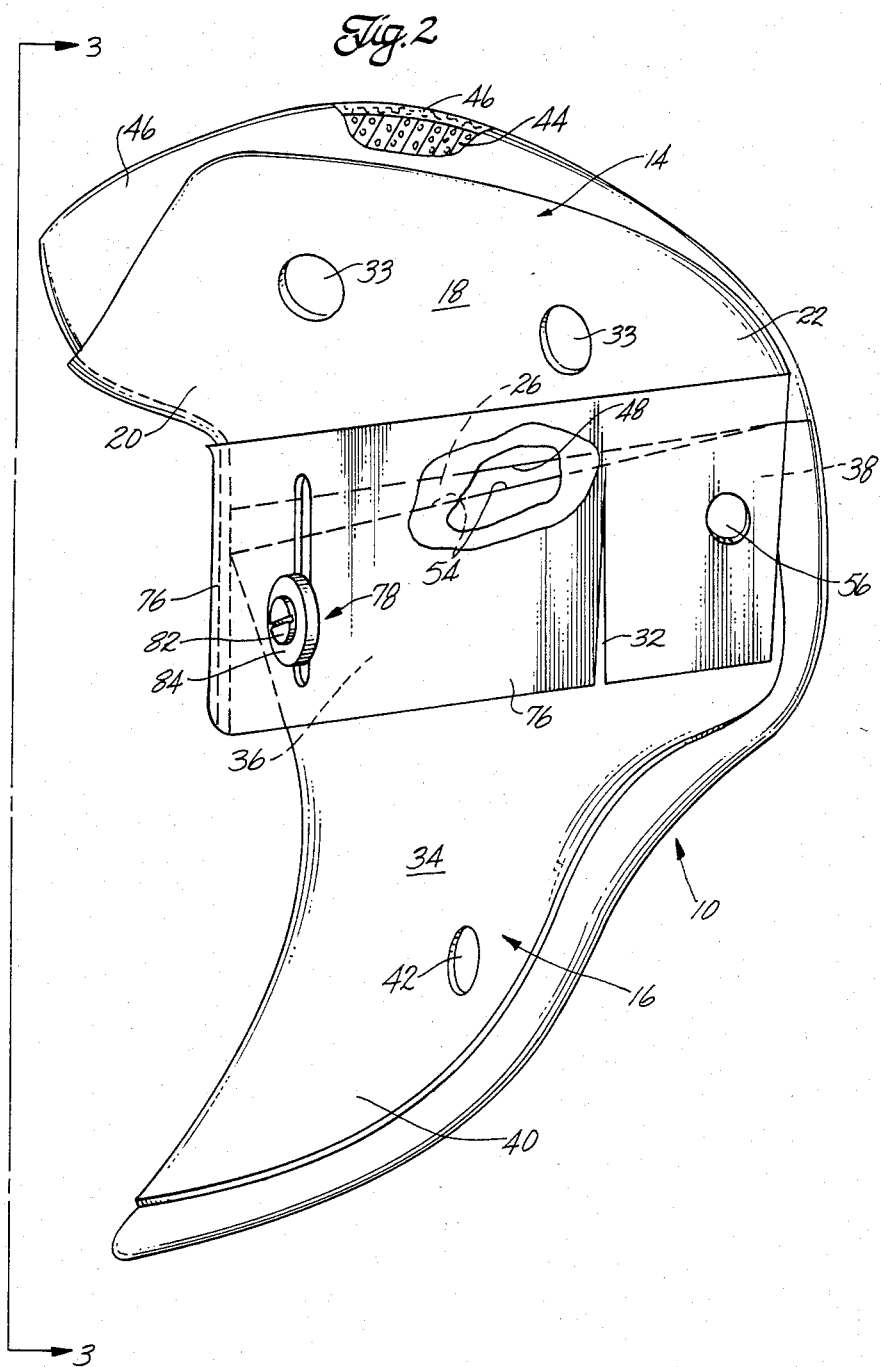
FIG. 2 is a side elevation view, partly in cross section and partly broken away, showing the front half of the cervical collar.

A cervical collar according to principles of this invention includes a generally U-shaped front half 10 for supporting the chin region of a patient and a generally U-shaped rear half 12 for supporting the rear or occipital portion of the patient's head. The front half 10 of the collar is in the form of a shell which is split into upper and lower sections comprising a chin-supporting upper section 14 and a lower section 16 that fits around the lower portion of the patient's neck and rests on the front of the collarbone and the upper chest region of the patient.

The chin-supporting upper section 14 is made from a semi-rigid self-supporting shell 18 of a material preformed to conform to an anatomical shape that can support the underside of the chin region of the patient. The upper shell 18 is preferably made from a thin sheet of polyethylene that is sufficiently flexible to be vacuum-formed into the desired shape which remains reasonably flexible after shaping. The chin-supporting upper shell 18 has an elongated upwardly opening U-shaped portion 20 for extending under and along the sides of the patient's chin. The upper portion of the shell 18 extends to rear portions 22 for overlying rear portions of the patient's lower jaw. The lower portion of the upper shell 18 formed as a generally U-shaped reinforcing bridge member 24 (it is U-shaped when viewed from above) which overlaps a narrow slot 26 formed as a split between the upper and lower sections of the collar front half. The bridge member 24 is an integral part of the upper shell 18 and extends below the upper front and rear portions 20 and 22 in a manner akin to a generally vertical skirt. The bridge member is reasonably flexible laterally, but is substantially stiff longitudinally. The upper shell 18 is formed so that the bridge member extends generally normal to the chin and jaw-supporting upper portions of the shell, so that the stiffness of the bridge member provides stiff support resisting downward forces on the chin and jaw-supporting portions of the upper shell. The U-shaped bridge member is partially split by a central groove 28 in its front lower edge. This groove permits the U-shaped member to flex lengthwise and laterally when the upper section 14 is moved relative to the lower section 16. Added flexibility can be provided by additional grooves 30 and 32 near the rear portions of the U-shaped reinforcing member. Air holes 33 are formed in the upper shell.

The lower section 16 of the collar front half is made from a thin, semi-rigid shell 34 that has been preformed to conform to the contour of the lower portion of the patient's neck and the front portion of the collarbone and upper central portion of the patient's chest region. The lower shell 34 is preferably made from the same material as the upper shell 18. It is preferably vaccum-formed from a thin flexible but self-supporting sheet of material such as polyethylene. The lower shell 34 has a U-shaped (when viewed from above) upper portion 36 for conforming to the shape of the lower portion of the patient's neck. This portion of the shell extends rearwardly along both sides of the patient's neck to end regions 38 below the end portions of the patient's lower jaw. The lower shell 34 flares outwardly to the sides and forwardly and downwardly below the U-shaped upper portion 36 to form a generally U-shaped (when viewed from the front) lower portion 40 shaped to conform to the front portion of the collarbone and the upper central region of the patient's chest. Air holes 42 are formed in the lower shell 34.

A layer of padding covers the inside face of the upper shell 18. The layer preferably comprises an internal layer 44 of an open cell resilient plastic foam material such as polyurethane foam. The open cell foam material is used because the open cell material is capable of "breathing", i.e., it allows air circulation through the cells and absorbs moisture, as opposed to a closed cell material which does not breathe appreciably and which does not absorb fluids to any significant extent.

The open cell foam layer is enclosed within an outer layer 46 of a soft flexible fabric that is also capable of breathing and is comfortable when in direct contact with the skin for long periods of time. A preferred outer layer material is velour. The enclosure formed by the velour is preferably made by overlaying two pieces of velour on opposite faces of the open cell foam layer and then fastening the overlying layers of velour by stitching around the entire outer perimeter of the foam layer. The resulting padding is then affixed to the inside face of the upper shell by a suitable adhesive. The padding covers the chin-supporting portion of the upper shell 18 and terminates at a lower edge 48 which extends across the lower portion of the U-shaped chin-supporting portion of the upper shell, leaving the inside face of the bridge member free of such padding.

A similar layer of padding covers the inside face of the lower shell 34. The padding on the lower shell preferably comprises a similar internal layer 50 of a resilient open cell plastic foam material such as polyurethane foam enclosed within outer layers 52 of velour. The padding that covers the inside face of the lower shell terminates at an upper edge 54 adjacent the lower edge 48 of padding on the upper shell.

Figure 1:
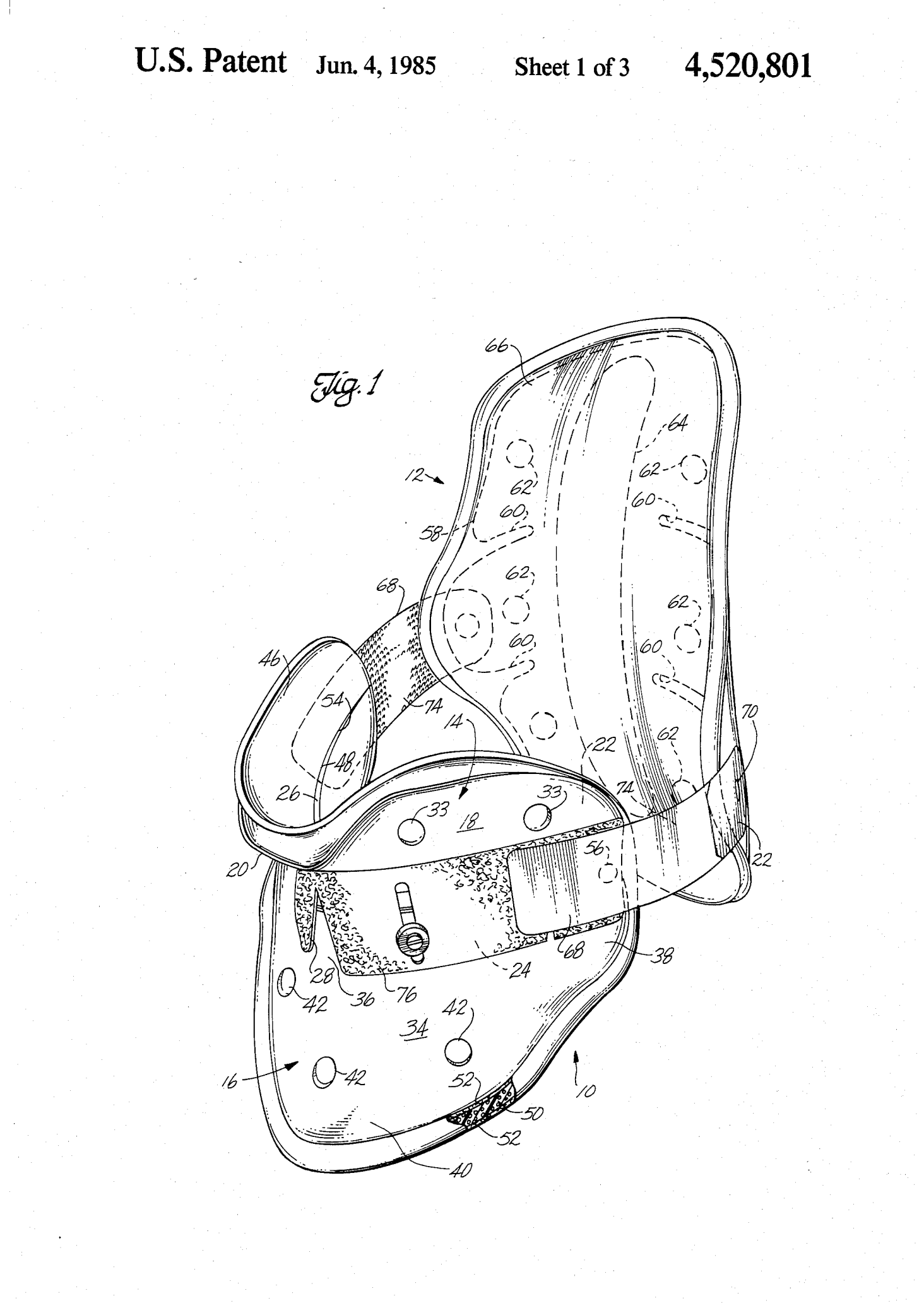
Figure 3:
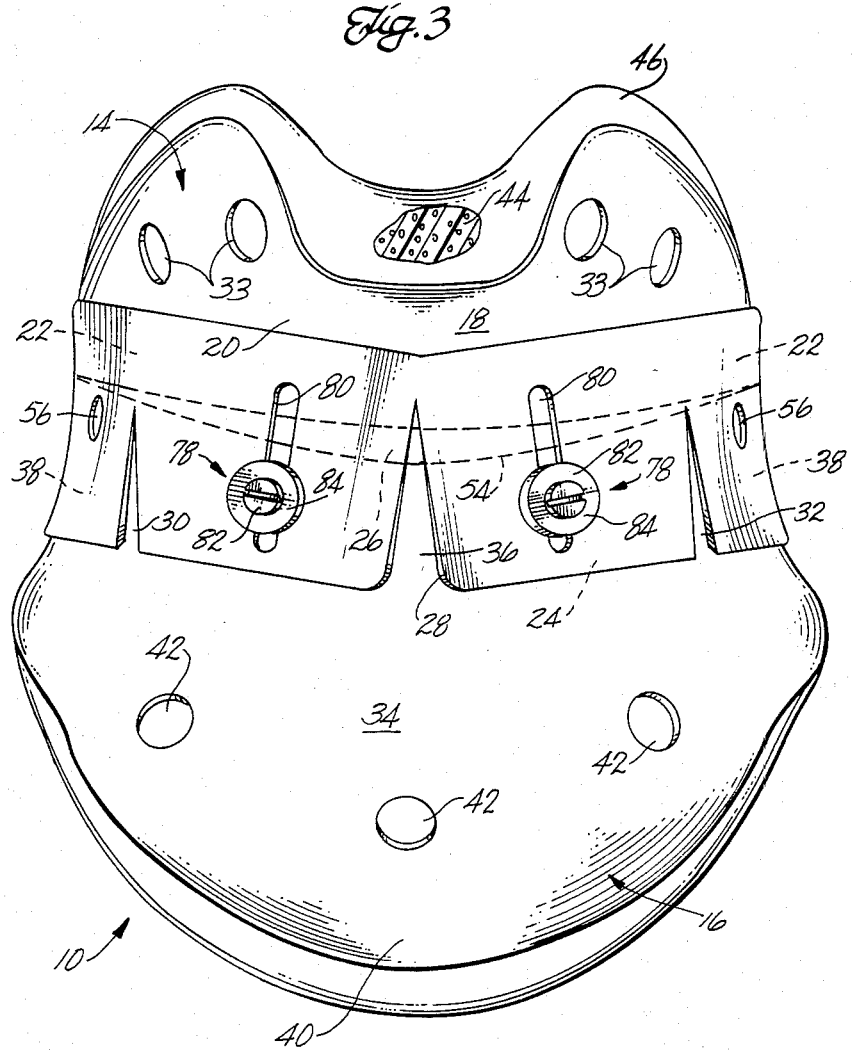
FIG. 3 is a front elevation view, partly broken away, taken on line 3—3 of FIG. 2.

The upper and lower sections 14, 16 of the collar front half are hinged to each other so that one section is movable toward or away from the other section. The two sections are hinged to each other by a pair of rivets 56 that pivot the rear lower jaw regions of the upper and lower sections 14, 16 to each other. The two sections are secured so that the elongated bridge member 24 of the upper shell 18 overlaps the upper portions 36 of the lower shell 34. The rivets attach the opposite rear portions of the bridge member 24 to the upper rear portions 38 of the lower shell. The bridge member thus forms a U-shaped (when viewed from above) piece that overlies the U-shaped upper portion 36 of the lower shell continuously from the rear lower jaw region on one side, around the front of the patient's neck, to the rear lower jaw region on the other side of the patient. The hinging of the upper and lower sections allows the two sections to pivot through an angle about a transverse axis through the rivets. This allows the upper and lower sections to pivot through infinitely adjustable angular positions relative to one another which either widens or closes the split 26 between the two sections. The two sections pivot between a closed position, in which the bridge member has its maximum overlap on the upper portion 36 of the lower shell, to a fully open position in which the overlap of the bridge member is at its minimum. In the closed position, the confronting lower and upper edges 48, 54 of the padding are in contact with each other. As the two sections are pivoted apart toward the fully open position, the tapered gap 26 between the edges of the padding is widened. The position of the cervical collar shown in FIGS. 1 through 3 is near the fully open position of the collar.

The rear half 12 of the collar includes a semi-rigid shell 58 preferably made from a thin self-supporting but flexible plastic piece such as polyethylene. The shell 58 is shaped to conform to the slightly U-shaped shallow curvature of the head from the occipital region down along the rear of the neck to the upper shoulder region. Narrow slots 60 are formed in opposite sides of the rear shell 58 to add flexibility. Air holes 62 also are formed in the shell. A metal reinforcing bar 64 extends along the vertical centerline of the rear shell to add rigidity. The reinforcing bar is made of a malleable metal such as aluminum so that it can be shaped to conform to the curvature of the patient's rear neck region. A layer of resilient padding 66 covers the inside face of the shell 58. The padding is made from a material similar to the padding that covers the inside faces of the upper and lower sections 14 and 16 of the front half fo the collar, i.e., a resilient open cell plastic foam material such as polyethylene internally within outer layers of velour. The padding is affixed to the inside face of the shell 58 by a suitable adhesive.

A pair of flexible straps 68 are affixed to opposite sides of the rear half 12 of the collar. The flexible straps are preferably affixed by rivets 70 extending through vinyl reinforcing pieces 72. The flexible straps are preferably made of a strong flexible material such as nylon. The inside faces of the flexible straps have a thistle cloth fastener material 74, preferably a layer of Velcro hook-type material. In use the flexible straps 68 extend toward the U-shaped bridge member 24 on the front half 10 of the colalr so that the flexible straps can overly the bridge member. A layer 76 of a thistle cloth fastener material is affixed to the front face of the bridge member 24. Preferably, the fastener material 76 is Velcro pile type material. In use, the front and rear halves 10 and 12 of the cervical collar can be attached to one another by overlapping the free ends of the flexible straps over the bridge member and attaching the cooperating Velcro surfaces to hold the front and rear halves of the collar in place.

A pair of fastening and guide means 78 hold the upper and lower sections 14 and 16 of the collar front half in the desired angular position and guide the angular travel between the two sections. The fastening and guide means include a pair of laterally spaced apart narrow, elongated right and left slots 80 formed in the front central portion of the bridge member 24. The right and left slots are generally parallel to one another and extend generally vertically from near the chin supporting portion of the upper shell downwardly toward the bottom edge of the bridge member. During use the two slots extend generally vertically over the right and left front central portions of the patient's neck. Separate posts (not shown) extend through the guide slots 80. Each post is preferably formed by a rivet affixed to the underside of the U-shaped upper region 36 of the lower shell. Each rivet has an internally threaded shank which extends through a corresponding guide slot 80. A pair of screws 82, each carrying a washer 84, are threaded into the internally threaded shanks of the rivets that extend through the slots 80. The screws can be loosened to allow the upper and lower sections 12 and 14 to pivot through an angle to the desired angular position between them. The screws then can be tightened to apply force to the front face of the bridge member through the washers for holding the two sections in the desired angular position. The shank portions of the rivets act as posts to cooperate with the guide slots to guide angular travel between the upper and lower sections.

The cervical collar is used by placing the upper section 14 of the collar front half 10 under the patient's chin and supporting it by the lower section 16 which rests on the patient's collarbone region and the upper central portion of the patient's chest region. The upper and lower sections 14 and 16 are adjusted to the patient's neck size by adjusting the angle between the upper and lower sections. The screws 82 are loosened to pivot the two sections relative to one another to the desired angular setting. The screws are tightened to hold the upper and lower sections in the desired position. The rear half 12 of the collar is then placed against the rear occipital region of the patient and the lower portion of this section is supported at the rear upper central portion of the patient's shoulder region. The flexible straps 68 are then extended forward around opposite sides of the patient's neck and are attached to the Velcro fastener on the bridge member that extends under the patient's neck. In use, the rigidity provided by the bridge member, as it is held in a fixed position by the fasteners, provides support for the chin-supporting portion of the collar. This rigid support is provided independently of the angular setting of the collar. The open cell foam padding allows the padded portions of the cervical collar to breathe which provides comfort for the patient during long periods of use.

What is claimed is:

1. A cervical collar having an improved chin support comprising:

an upper section formed as a thin, semi-rigid upper shell having (a) a generally U-shaped chin-supporting front portion shaped to conform to a patient's chin and having side portions extending along the patient's lower jaw to rear portions in the vicinity of the rear lower jaw, and (b) a generally U-shaped lower bridge member having side portions extending along opposite sides of the patient's neck and a front portion extending across the front of the patient's neck, the bridge member extending generally normal to the U-shaped chin supporting portion of the upper section; and a layer of a resilient open cell containing material on an inside face of the upper portion of the shell;

a lower section formed as a thin, semi-rigid lower shell having an upper portion for overlying the lower portion of the patient's neck generally around the vicinity of the collar bone, and a lower portion for resting on a front portion of the patient's chest region; and a layer of a resilient open cell containing material on an inside face of the lower shell;

means attaching the upper and lower sections to one another so that one section is movable relative to the other and for retaining the two sections affixed to each other with the bridge member overlapping the upper portion of the lower section, the two sections being movable to adjust the distance the lower section can be moved toward or away from the upper section to adjust the combined upper and lower sections to different neck sizes; and fastening means extending between the bridge member and the upper portion of the lower section for being loosened to allow said relative movement between the two sections and for being tightened to hold the two sections in a desired relative position, with the fixed bridge member providing a reinforcing bridge between the upper portion of the lower section and the chin-supporting portion of the upper section.

2. Apparatus according to claim 1 in which the portion of the bridge member that overlaps the lower shell is unpadded; and the padding on the upper and lower shells forms a split which is widened when the upper and lower shells are moved farther apart and narrowed when the two shells are moved closer toward each other.

3. Apparatus according to claim 2 in which the fastening means includes guide means for guiding travel between the two shells.

4. Apparatus according to claim 3 in which the guide means include elongated slots formed in the bridge member; and in which the fastening means include separate posts extending through the guide slots, and fasteners engaged with the posts for being loosened or tightened to hold the bridge member in a fixed position relative to the lower shell.

5. Apparatus according to claim 1 in which the cervical collar includes a rear support for the rear portion of the patient's head, flexible straps on opposite sides of the rear support, fastening means on the straps, and cooperating fastening means on the bridge member.

6. A cervical collar having an improved chin support comprising:
   a preformed semi-rigid shell in an anatomical shape that conforms to the chin region, the front portion of the neck, the front region of the collarbone, and the upper chest region, the shell being split into a chin-supporting upper section and a lower section;
   means for securing the upper and lower sections to each other so that the two sections are movable relative to each other to widen or narrow a split between them for adjusting the shape of the shell to the size of the patient's chin and neck region;
   a generally U-shaped bridge member extending along the spacing and bridging the distance between the upper and lower sections of the shell;
   fastening means for holding the bridge member in a preset position relative to the upper and lower sections for holding the upper and lower sections in a desired adjustable position, with the stiffness of the bridge member providing support for the chin-supporting upper section of the shell independently of the preset position of the bridge member; and
   a layer of an open cell containing material on the inside face of the shell.

7. Apparatus according to claim 6 in which the bridge member is part of the chin-supporting upper section of the shell and overlies the upper portion of the lower section of the shell; and the fastening means extend between the bridge member and said upper portion of the lower section of the shell.

8. Apparatus according to claim 7 in which the bridge member does not have said layer of material but directly overlies the face of the lower section of the shell.

9. A cervical collar having an improved chin support comprising:
   a thin-walled preformed semi-rigid shell in an anatomical shape that conforms to the chin region, the front portion of the neck, the front region of the collar-bone, and the upper chest region, the shell being split into a chin-supporting upper section and a lower supporting section;
   means for securing the upper and lower sections of the shell to each other so that the two sections are movable relative to each other to widen or narrow a space between them for adjusting the shape of the shell to the size of the patient's chin and neck region;
   a generally U-shaped bridge member extending over said space for bridging the distance between the upper and lower sections of the shell; and
   fastening means for holding the bridge member in a preset position relative to the upper and lower sections of the shell for holding the upper and lower sections in a desired adjustable position, with the stiffness of the bridge member providing a rigid lower support means for the chin-supporting upper section of the shell independently of the preset position of the bridge member.

10. Apparatus according to claim 9 in which the bridge member is part of the chin-supporting upper section of the shell and overlies the lower supporting section of the shell; and the fastening means extends between the bridge member and the lower section of the shell.

11. Apparatus according to claim 9 in which the fastening means includes guide means for guiding travel between the upper and lower sections of the shell.

12. Apparatus according to claim 11 in which the guide means include elongated slots formed in the bridge member; and in which the fastening means include separate posts extending through the guide slots, and fasteners engaged with the posts for being loosened or tightened to hold the bridge member in a fixed position relative to the lower supporting section of the shell.

* * * * *